US007369638B2

(12) United States Patent
Kiraly et al.

(10) Patent No.: US 7,369,638 B2
(45) Date of Patent: May 6, 2008

(54) SYSTEM AND METHOD FOR DETECTING A PROTRUSION IN A MEDICAL IMAGE

(75) Inventors: Atilla Peter Kiraly, Plainsboro, NJ (US); Carol L. Novak, Newtown, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 187 days.

(21) Appl. No.: 10/849,576

(22) Filed: May 19, 2004

(65) Prior Publication Data

US 2005/0008205 A1 Jan. 13, 2005

Related U.S. Application Data

(60) Provisional application No. 60/486,799, filed on Jul. 11, 2003.

(51) Int. Cl.
*A61B 6/03* (2006.01)
(52) U.S. Cl. .......................... 378/4; 378/901; 382/131; 382/199
(58) Field of Classification Search .................. 378/4, 378/8, 15, 19, 62, 901; 382/128, 131, 154, 382/199
See application file for complete search history.

(56) References Cited

U.S. PATENT DOCUMENTS

| 5,452,367 | A  | * | 9/1995  | Bick et al.  | 382/128 |
| 6,470,092 | B1 | * | 10/2002 | Li et al.    | 382/132 |
| 2002/0164061 | A1 |   | 11/2002 | Paik et al. |         |

OTHER PUBLICATIONS

Gibson, Sarah F.F., Using Distance Maps for Accurate Surface Representation in Sampled Volumes, *IEEE* 1998.
Yoshida Hiroyuki et al., "Three-Dimensional Computer-Aided Diagnosis Scheme for detection of Colonic Polyps," *IEEE Transactions on Medical Imaging* 20:Dec. 12, 2001 XP-001101455.
Göktük et al., "A Statistical 3-D Pattern Processing Method for Computer-Aided Detection of Polyps in CT Colonography;" *IEEE Transactions on Medical Imaging* 20:Dec. 12, 2001; XP-002303576.
Kiss Gabriel et al. "Computer Aided Diagnosis for Virtual Colonography;" XP002308817, 2001.
International Search Report for PCT/US2004/016108 mailed Jan. 18, 2005.

* cited by examiner

*Primary Examiner*—Chih-Cheng G Kao
(74) *Attorney, Agent, or Firm*—David B. Paschburg; F. Chau & Associates, LLC (57) ABSTRACT

A method for detecting a protrusion in a medical image includes: acquiring a medical image, wherein the medical image is of an anatomical part; segmenting the medical image; calculating a distance map of the medical image; calculating a gradient of the distance mapped medical image; and processing the gradient to detect a protrusion in the medical image. The gradient is processed by: projecting a plurality of rays from a location in the distance mapped medical image; calculating a value for each of the plurality of rays based on features of each of the plurality of rays and the gradient of the distance mapped medical image; summing and scaling the value of each of the plurality of rays; and detecting one of a sphere-like and polyp-like shape using the summed and scaled values of the plurality of rays, wherein one of the sphere-like and polyp-like shapes is the protrusion.

26 Claims, 7 Drawing Sheets

SYSTEM AND METHOD FOR DETECTING A PROTRUSION IN A MEDICAL IMAGE

CROSS-REFERENCE TO RELATED APPLICATIONS

This application claims the benefit of U.S. Provisional Application No. 60/486,799, filed Jul. 11, 2003, a copy of which is herein incorporated by reference.

BACKGROUND OF THE INVENTION

1. Technical Field

The present invention relates to a system and method for detecting a protrusion in a medical image and, more particularly, to detecting a protrusion in a medical image by calculating a distance map of a segmented medical image and processing gradient characteristics of the distance mapped medical image to detect a protrusion in the medical image.

2. Discussion of the Related Art

In the field of medical imaging, various systems have been developed for generating medical images of various anatomical structures of individuals for the purposes of screening and evaluating medical conditions. These imaging systems include, for example, computed tomography (CT) imaging, magnetic resonance imaging (MRI), positron emission tomography (PET), etc. Each imaging modality may provide unique advantages over other modalities for screening and evaluating certain types of diseases, medical conditions or anatomical abnormalities, including, for example, colonic polyps, aneurysms, lung nodules, calcification on heart or artery tissue, cancer micro-calcifications or masses in breast tissue, and various other lesions or abnormalities.

For example, CT imaging systems can be used to obtain a set of cross-sectional images or two-dimensional (2D) "slices" of a region or interest (ROI) of a patient for purposes of imaging organs and other anatomies. The CT modality is commonly employed for purposes of diagnosing disease because such a modality provides precise images that illustrate the size, shape, and location of various anatomical structures such as organs, soft tissues, and bones, and enables a more accurate evaluation of lesions and abnormal anatomical structures such as cancer, polyps, etc.

One conventional method that physicians, clinicians, radiologists, etc., use for diagnosing and evaluating medical conditions is to manually review hard-copies (X-ray films, prints, photographs, etc.) of medical images that are reconstructed from an acquired dataset, to discern characteristic features of interest. For example, CT image data that is acquired during a CT examination can be used to produce a set of 2D medical images (X-ray films) that can be viewed to identify potential abnormal anatomical structures or lesions by a trained physician, clinician, radiologist, etc. A virtual colonoscopy may produce medical images that include normal anatomical structures corresponding to the colon, and a trained radiologist may be able to identify small polyps among these structures that are potentially cancerous or pre-cancerous. However, a trained physician, clinician or radiologist may overlook a medical condition such as colonic polyps due to human error.

Accordingly, various image processing systems and tools have been developed to assist physicians, clinicians, radiologists, etc. in evaluating medical images to diagnose medical conditions. For example, computer-aided detection (CAD) tools have been developed for various clinical applications to provide automated detection of medical conditions in medical images. In general, CAD systems employ methods for digital signal processing of image data (e.g., CT data) to automatically detect colonic polyps and other abnormal anatomical structures such as lung nodules, lesions, aneurysms, calcification on heart or artery tissue, micro-calcifications or masses in breast tissue, etc.

Although such CAD systems are very useful for diagnostic purposes, cost-reduction is difficult to achieve as the amount of data, for example, a radiologist, has to examine is abundant thus leading to lengthy analysis time and high costs of professional charges for the radiologist's interpretation. In addition, many CAD systems suffer from false positives (e.g., incorrectly identifying normal tissues as abnormal) and false negatives (e.g., failing to correctly identify abnormalities). Accordingly, there is a need for a CAD technique that identifies medical conditions such as colonic polyps in medical images accurately so that a medical expert such as a radiologist can efficiently and correctly analyze these conditions in a short amount of time.

SUMMARY OF THE INVENTION

The present invention overcomes the foregoing and other problems encountered in the known teachings by providing a system and method for detecting a protrusion in a medical image.

In one embodiment of the present invention, a method for detecting a protrusion in a medical image comprises: segmenting a medical image; calculating a distance map of the medical image; calculating a gradient of the distance mapped medical image; and processing the gradient to detect a protrusion in the medical image.

The method further comprises: acquiring the medical image, storing a list of one or more detected protrusions; and filtering one or more false positives from the list, wherein one or more of the false positives is a not one of a nodule, lesion, polyp, pre-cancerous growth, and cancerous growth. The medical image is acquired by one of a computed tomographic (CT), helical CT, x-ray, positron emission tomographic, fluoroscopic, ultrasound, and magnetic resonance (MR) imaging technique. The medical image is of an anatomical part. The protrusion is one of a nodule, lesion, polyp, pre-cancerous growth, and cancerous growth.

The processing step further comprises: projecting a plurality of rays from a location in the distance mapped medical image; calculating a value for each of the plurality of rays based on features of each of the plurality of rays and the gradient of the distance mapped medical image; summing and scaling the value of each of the plurality of rays; and detecting one of a sphere-like and polyp-like shape using the summed and scaled values of the plurality of rays, wherein one of the sphere-like and polyp-like shapes is the protrusion.

The processing step may also comprise: projecting a plurality of rays from a location comprising an original distance value in the distance mapped medical image; calculating an absolute value of a difference between a length of each of the plurality of rays and a distance value at an end of each of the plurality of rays, wherein the length of each of the plurality of rays is a fraction of the original distance value from the location; dividing a sum of the absolute values by the total number of the plurality of rays; and detecting one of a sphere-like and polyp-like shape using the division result, wherein one of the sphere-like and polyp-like shapes is the protrusion.

In another embodiment of the present invention, the processing step comprises: projecting a plurality of rays from a location comprising an original distance value in the distance mapped image; determining a distance value for each of the plurality of rays that is a fraction of the distance from the location; calculating a sphere-based response, wherein the sphere-based response is calculated by:

$$\frac{\sum_{i \in S}(d - l_i)}{T}$$

where d is the original distance value, $l_i$ is the length of a ray i, T is a total number of the plurality of rays, and S is a set of the plurality of rays such that $l_i < d$; and detecting the protrusion using the sphere-based response.

In yet another embodiment of the present invention, the processing step comprises: projecting a plurality of rays from a location comprising an original distance value in the distance mapped medical image; determining a distance value for each of the plurality of rays that has a supplementary ray that has a distance value less than the original distance value; calculating a hemisphere-based response, wherein the hemisphere-based response is calculated by:

$$\frac{\sum_{i \in S}(d - l_i)}{T/2}$$

where d is the original distance value, $l_i$ is the length of a ray i, T is a total number of the plurality of rays, and S is a set of the plurality of rays whose supplementary rays do not have a value less than the original distance value; and detecting the protrusion using the hemisphere-based response.

The processing step additionally comprises: projecting a plurality of rays from an edge of the distance mapped medical image, wherein the plurality of rays follows the steepest gradient; and accumulating paths of the plurality of rays, wherein the accumulated paths form a response image for detecting the protrusion. The processing step further comprises: projecting a plurality of rays from a location comprising an original distance value in the distance mapped medical image; determining a distance value for each of the plurality of rays that is a fraction of the distance from the location; calculating a sphere-based response, wherein the sphere-based response is calculated by:

$$\frac{\sum_{i=0}^{F \times d}|d_i - l_i|}{T}$$

where d is the original distance value, F is a fractional value between 0 and 1, $d_i$ is the distance value at a point along one of the plurality of rays, $l_i$ is the length of one of the plurality of rays at a point i, and T is the total number of points taken from i=0 to i=F*d; calculating a gray-level difference of the distance mapped medical image, wherein the gray level difference is calculated by:

$$\frac{\sum_{i=0}^{K} r_k}{K}$$

where rk represents the sphere-based response for a ray k; and detecting the protrusion using the gray-level difference.

In another embodiment of the present invention, a system for detecting a protrusion in a medical image comprises: a memory device for storing a program; a processor in communication with the memory device, the processor operative with the program to: segment a medical image; calculate a distance map of the medical image; calculate a gradient of the distance mapped medical image; and process the gradient to detect a protrusion in the medical image.

The processor is further operative with the program code when processing the gradient to: project a plurality of rays from a location comprising an original distance value in the distance mapped medical image; determine a distance value for each of the plurality of rays that is a fraction of the distance from the location; calculate a sphere-based response of the plurality of rays; calculate a hemisphere-based response of the plurality of rays; and detect the protrusion using the sphere and hemisphere-based responses.

In yet another embodiment of the present invention, the processor is further operative with the program code when processing the gradient to: project a plurality of rays from a location comprising an original distance value in the distance mapped medical image; determine a distance value for each of the plurality of rays that is a fraction of the distance from the location; calculate a sphere-based response of the plurality of rays; calculate a gray-level difference of the distance mapped medical image; and detect the protrusion using the sphere-based response and the gray-level difference.

In another embodiment of the present invention, a computer program product comprising a computer useable medium having computer program logic recorded thereon for detecting a protrusion in a medical image, the computer program logic comprises: program code for segmenting a medical image; program code for calculating a distance map of the medical image; program code for calculating a gradient of the distance mapped medical image; and program code for processing the gradient to detect a protrusion in the medical image.

In yet another embodiment of the present invention, a system for detecting a protrusion in a medical image comprises: means for acquiring a medical image; means for segmenting the acquired medical image; means for calculating a distance map of the medical image; means for calculating a gradient of the distance mapped medical image; and means for processing the gradient to detect a protrusion in the medical image.

In another embodiment of the present invention, a method for detecting a polyp in an image of a colon comprises: acquiring the image of the colon; segmenting a surface of the colon from a nearby structure; calculating a distance map of the segmented surface; calculating a gradient of the distance mapped image; and processing the gradient to detect the polyp in the colon, wherein the gradient is processed by: projecting a plurality of rays from a location in the distance mapped image; calculating a value for each of the plurality of rays based on features of each of the plurality of rays and the gradient of the distance mapped image; summing and scaling the value for each of the plurality of rays; and detecting one of a sphere-like and polyp-like shape using the summed and scaled values of the plurality of rays, wherein one of the sphere-like and polyp-like shapes is the polyp.

The foregoing advantages and features are of representative embodiments and are presented to assist in understanding the invention. It should be understood that they are not intended to be considered limitations on the invention as defined by the claims, or limitations on equivalents to the claims. Therefore, this summary of features and advantages should not be considered dispositive in determining equivalents. Additional features and advantages of the invention will become apparent in the following description, from the drawings and from the claims.

DETAILED DESCRIPTION OF EXEMPLARY EMBODIMENTS

Figure 1:
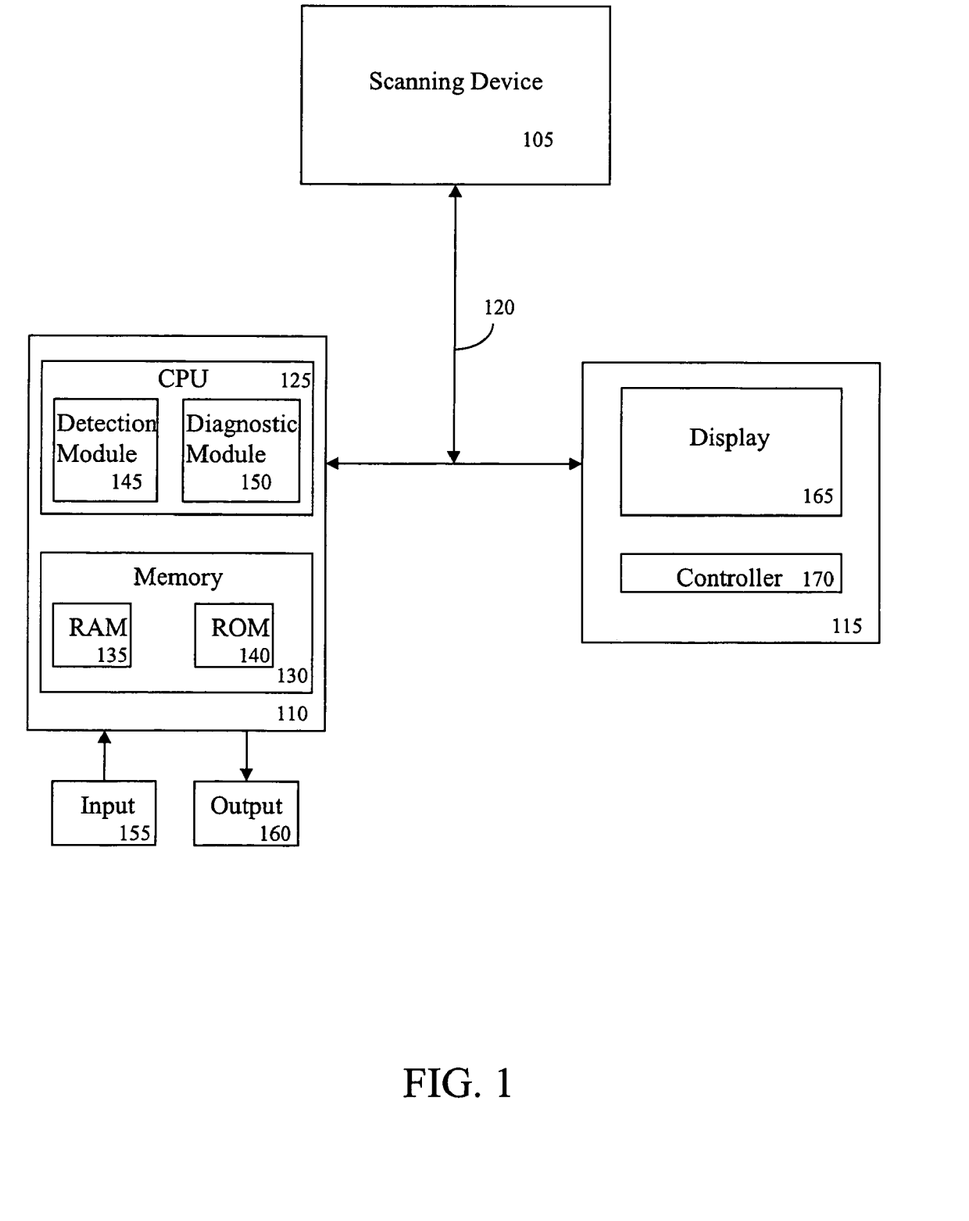
FIG. 1 is a block diagram of a system for detecting a protrusion in a medical image according to an exemplary embodiment of the present invention.

FIG. 1 is a block diagram of a system 100 for detecting a protrusion in a medical image according to an exemplary embodiment of the present invention. As shown in FIG. 1, the system 100 includes, inter alia, a scanning device 105, a personal computer (PC) 110 and an operator's console 115 connected over, for example, an Ethernet network 120. The scanning device 105 may be a magnetic resonance imaging (MRI) device, a computed tomography (CT) imaging device, a helical CT device, a positron emission tomography (PET) device, a two-dimensional (2D) or three-dimensional (3D) fluoroscopic imaging device, a 2D, 3D, or four-dimensional (4D) ultrasound imaging device, or an x-ray device, etc.

The PC 110, which may be a portable or laptop computer, a personal digital assistant (PDA), etc., includes a central processing unit (CPU) 125 and a memory 130, which are connected to an input 155 and an output 160. The CPU 125 includes a detection module 145, which is a computer-aided detection (CAD) module that includes one or more methods for detecting a protrusion, such as a polyp, in a medical image. The CPU 125 further includes a diagnostic module 150, which is used to perform automated diagnostic or evaluation functions of medical image data.

The memory 130 includes a random access memory (RAM) 135 and a read only memory (ROM) 140. The memory 130 can also include a database, disk drive, tape drive, etc., or a combination thereof. The RAM 135 functions as a data memory that stores data used during execution of a program in the CPU 125 and is used as a work area. The ROM 140 functions as a program memory for storing a program executed in the CPU 125. The input 155 is constituted by a keyboard, mouse, etc., and the output 160 is constituted by a liquid crystal display (LCD), cathode ray tube (CRT) display, printer, etc.

The operation of the system 100 is controlled from the operator's console 115, which includes a controller 170, for example, a keyboard, and a display 165, for example, a CRT display. The operator's console 115 communicates with the PC 110 and the scanning device 105 so that 2D image data collected by the scanning device 105 can be rendered into 3D data by the PC 110 and viewed on the display 165. It is to be understood that the PC 110 can be configured to operate and display information provided by the scanning device 105 absent the operator's console 115, using, for example, the input 155 and output 160 devices to execute certain tasks performed by the controller 170 and display 165.

The operator's console 115 may further include any suitable image rendering system/tool/application that can process digital image data of an acquired image dataset (or portion thereof) to generate and display 2D and/or 3D images on the display 165. More specifically, the image rendering system may be an application that provides 2D/3D rendering and visualization of medical image data, and which executes on a general purpose or specific computer workstation. Moreover, the image rendering system may include a graphical user interface (GUI), which enables a user to navigate through a 3D image or a plurality of 2D image slices. The PC 110 may also include an image rendering system/tool/application for processing digital image data of an acquired image dataset to generate and display 2D and/or 3D images.

As shown in FIG. 1, the detection module 145 and the diagnostic module 150 are also used by the PC 110 to receive and process digital medical image data, which as noted above, may be in the form of raw image data, 2D reconstructed data (e.g., axial slices), or 3D reconstructed data such as volumetric image data or multiplanar reformats, or any combination of such formats. The data processing results can be output from the PC 110 via the network 120 to an image rendering system in the operator's console 115 for generating 2D and/or 3D renderings of image data in accordance with the data processing results, such as segmentation of organs or anatomical structures, color or intensity variations, and so forth.

It is to be understood that CAD systems and methods according to the present invention for detecting protrusions in a medical image may be implemented as extensions or alternatives to conventional CAD methods or other automated detection methods for processing image data. Further, it is to be appreciated that the exemplary systems and methods described herein can be readily implemented with 3D medical images and CAD systems or applications that are adapted for a wide range of imaging modalities (e.g., CT, MRI, etc.) and for diagnosing and evaluating various abnormal anatomical structures or lesions such as colonic polyps, aneurysms, lung nodules, etc. In this regard, although exemplary embodiments may be described herein with reference to particular imaging modalities or particular anatomical features, nothing should be construed as limiting the scope of the invention.

It is to be further understood that the present invention may be implemented in various forms of hardware, software, firmware, special purpose processors, or a combination thereof. In one embodiment, the present invention may be implemented in software as an application program tangibly embodied on a program storage device (e.g., magnetic floppy disk, RAM, CD ROM, DVD, ROM, and flash memory). The application program may be uploaded to, and executed by, a machine comprising any suitable architecture.

Figure 2:
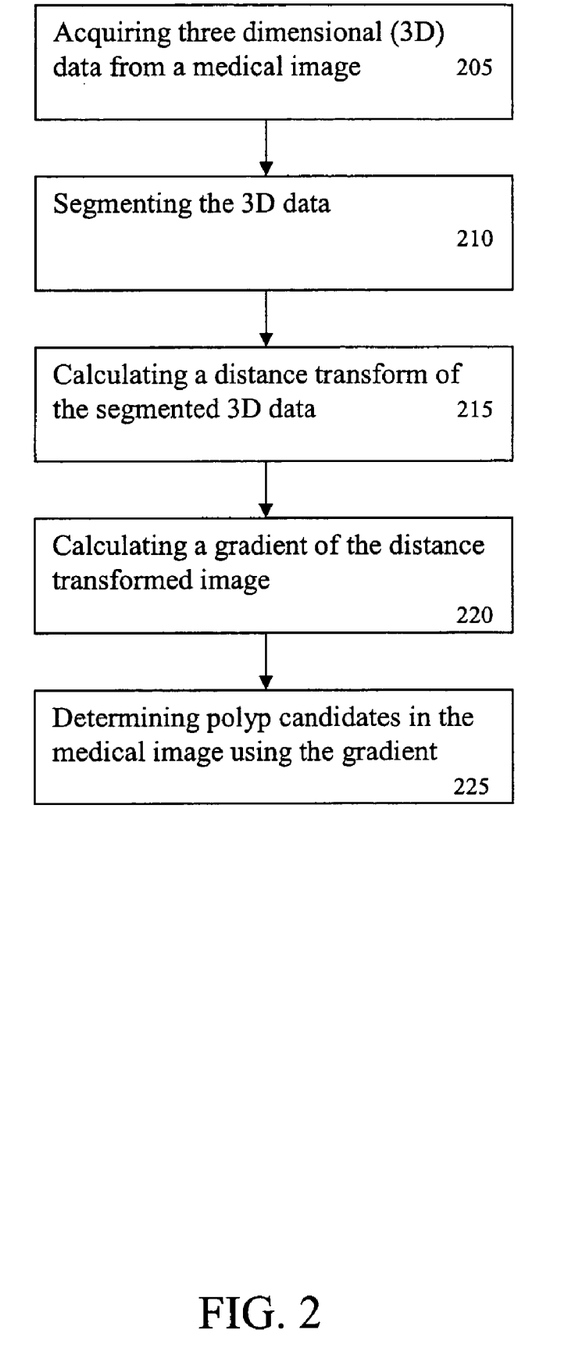
FIG. 2 is a flowchart showing an operation of a method for detecting a protrusion in a medical image according to an exemplary embodiment of the present invention.

FIG. 2 is a flowchart showing an operation of a method for detecting a protrusion in a medical image according to an exemplary embodiment of the present invention. As shown in FIG. 2, 3D data is acquired from a medical image of, for example, a colon (step 205). This is accomplished by using the scanning device 105, for example a CT scanner, operated at the operator's console 115, to scan the colon thereby generating a series of 2D images associated with the colon. The 2D images of the colon may then be converted or transformed into a 3D rendered image. It is to be understood that the medical image can be a lumen, which can be in addition to a colon, any one of a pancreas, a bronchi, a larynx, a trachea, a sinus, an ear canal, a blood vessel, a urethra and a bladder, etc. The medical image can also be a non-tubular structure, such as the lung-parenchyma or liver.

Figure 3:
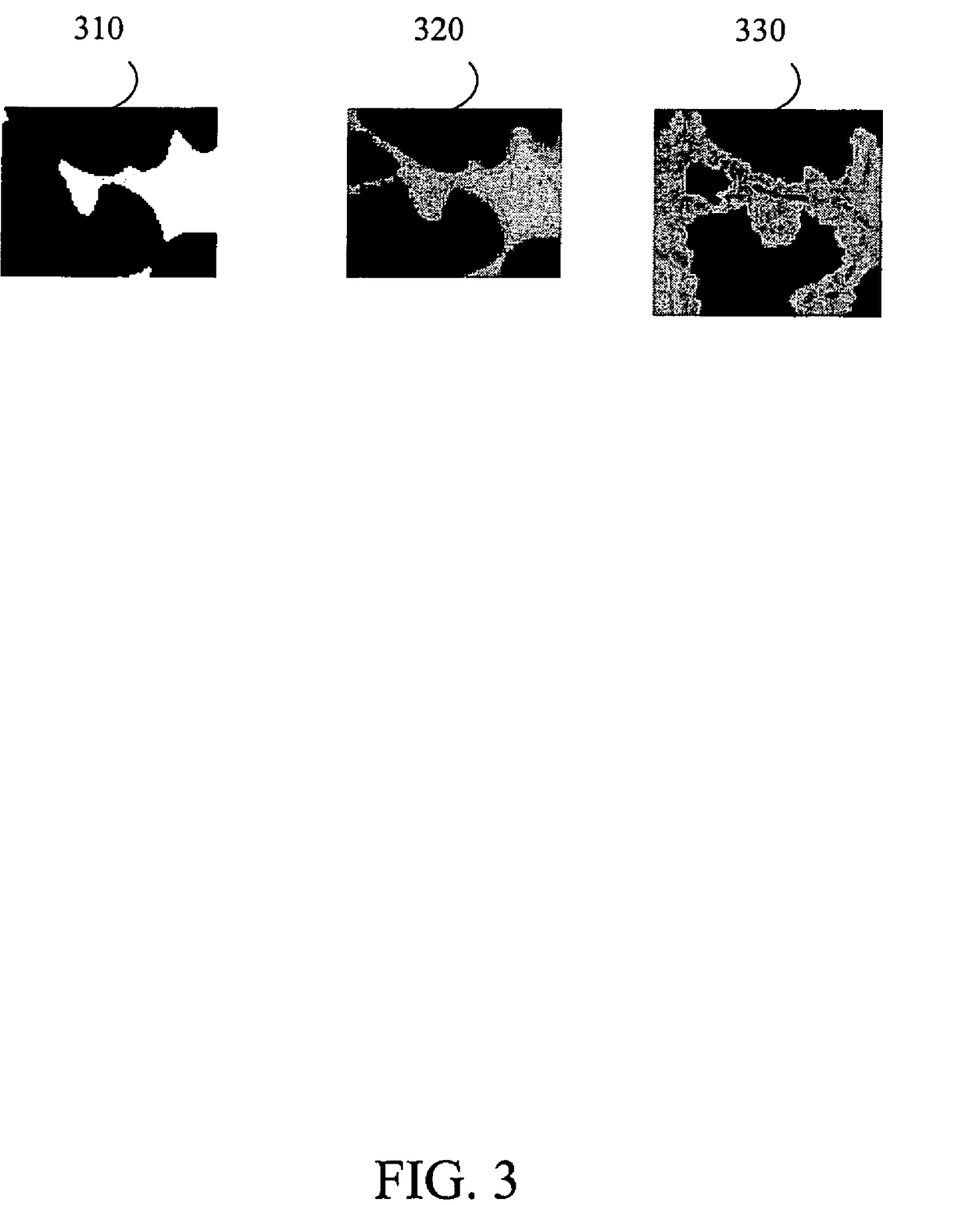
FIG. 3 illustrates three-dimensional (3D) medical images of a colon processed according to the method of FIG. 2.

After the 3D data is acquired from the colon, the 3D data of the colon is segmented (step 210). More specifically, a colon's surface or wall is segmented from other structures in the 3D image. As shown in FIG. 3, image 310 illustrates a portion of a colon after undergoing segmentation. In particular, the light portion of the image 310 defines the colon wall and the dark portion shows the colon lumen. It is to be understood that a variety of segmentation techniques may be used in accordance with the present invention, such as Region Growing, Thresholding, Gaussian Smoothing, Edge Detection, and Connected Component Labeling, to identify structures not belonging to the colon based upon, for example, size and location characteristics. In addition, not all segmentation methods for use with the present invention are limited only to colonic segmentation.

As further shown in FIG. 2, a distance transform and/or a distance map of the segmented 3D data is calculated (step 215). Several methods exist for computing distance transforms. One method, called the chamfer metric or the chamfer distance method, approximates a true Euclidean distance. In this method, the distance transform is calculated by first assigning all voxels outside of the lumen the value of infinity. The voxels of the colon wall and lumen are assigned a value of "0". These values correspond to distances from the lumen and will be updated by taking the smallest valued voxels, adding a distance value, and assigning the distance values to adjacent neighbors if the neighbors have greater values. This process is repeated until no new assignments occur.

Another method for computing the distance transform involves computing the true Euclidean distance, but at the cost of a greater processing time. Using a similar concept, neighbors are assigned values in the x, y, and z directions of an image. In each case, the square of the true voxel distance is assigned. As shown in FIG. 3, image 320 illustrates a distance transform of the image 310.

After calculating the distance transform of the segmented 3D data of the medical image, a gradient of the distance transform is acquired (step 220). The gradient of the distance transformed image is calculated using, for example, Equation (1) shown below:

$$\nabla I(x,y,z) = [dI(x,y,z)/dx,\ dI(x,y,z)/dy,\ dI(x,y,z)/dz] \qquad (1)$$

where I is the image, dI is the derivative of the image, and x, y, and z define a particular location in the image. It is to be understood that the gradient of the image can be computed in a variety of ways and, in one example, the gradient can be computed by convolving the image with a Gaussian-based kernel, thus resulting in a gradient that is less sensitive to image noise.

Subsequently, the distance transformed image is processed to determine polyp candidates (step 225). There are several methods discussed hereinafter with reference to FIGS. 3-7 that can be used to process the distance transformed and/or distance mapped image and provide polyp candidates.

Figure 4:
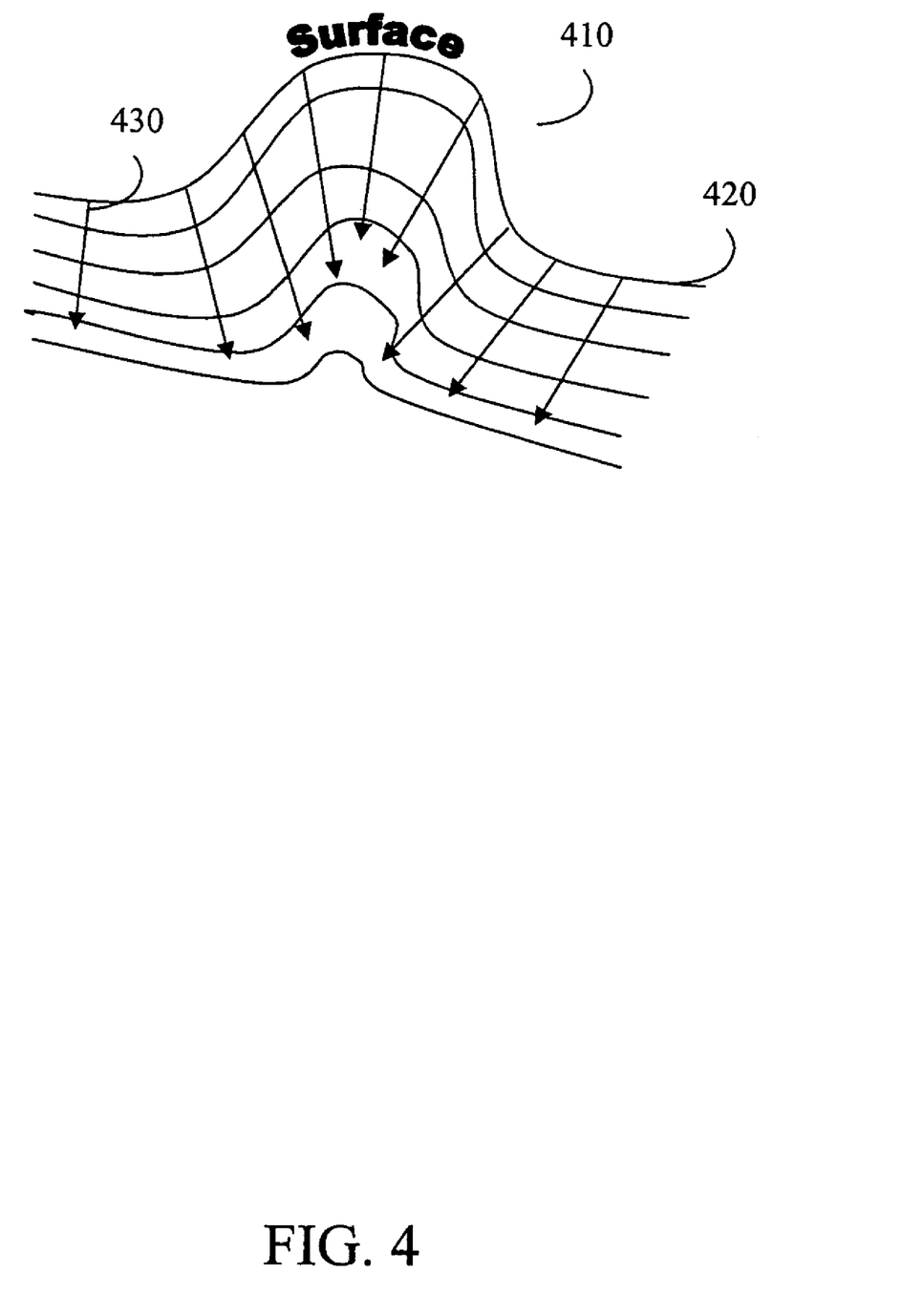
FIG. 4 illustrates a gradient of a 3D medical image converging with a center of a polyp-like structure in a colon.

It is observed that the calculated gradient of a distance transformed image tends to converge within a center of a polyp-like structure and/or shape, as shown, for example, in FIG. 4. In FIG. 4, a distance transformed image 410 has a polyp-like structure, lines 420 that illustrate a level of equal distance from the surface, and lines 430 that illustrate the direction of the calculated gradient of the distance transformed image 410.

In the first method, a series and/or plurality of rays are projected outward from a selected location in the distance transformed image, which can be any location where a polyp-like structure is located. A value (e.g., cosine values of the angle between the gradient and the plurality of rays) for each of the plurality of rays based on features (e.g., angles between the gradient and the plurality of rays or the length of each of the plurality of rays) of each of the plurality of rays and the gradient of the distance transformed image is calculated. The resulting value is summed and scaled and is used to determine a final value for the given location. The final value is then used to determine if the location has a sphere-like or polyp-like structure similar to that of a polyp.

Another method also involves using rays. For example, given a selected point (x,y,z) within an image, rays are cast radially outward from this location. When the rays hit a distance equal to a fraction (e.g., one quarter) of a distance label at its origin (i.e., the selected point from which the rays are cast), it is stopped. If the ray strikes a distance that is greater than its origin, it is counted as moving away from the segmented surface and is not considered. The absolute value of the ray length minus the distance at which the ray hits the fractional point and/or voxel is computed. The result is a sphere-ness value that reaches zero for a perfect sphere, and is used to determine if the location has a sphere-like or polyp-like structure similar to that of a polyp.

As shown in FIG. 3, image 330 illustrates the portion of the colon of image 320 after being processed using the first method described above to determine polyp candidates. More specifically, FIG. 3 illustrates taking bright portions of the processed image to determine polyp candidates. In this case, the polyp candidate is identified by the downward facing protrusion in the center of the image 330. In order to determine the candidates, a threshold of the image is taken, and only the voxels that are brighter than neighboring candidates are accepted, as the polyp candidates contain brighter voxel values than their neighbors.

After step 225, the detected protrusions are stored in the memory 130 of the CPU 125 for further analysis or they are immediately subject to analysis by, for example, a medical professional using a conventional CAD technique. During the analysis, the acquired data is filtered to determine if the detected protrusions are, for example, nodules, lesions, polyps, pre-cancerous growths, or cancerous growths. If they are not, they are filtered or removed from the data set and/or indicated as false positives.

In accordance with another exemplary embodiment of the present invention, the distance transformed image can undergo different processing methods to determine polyp candidates. For example, sphere and hemisphere-based responses, which tend to produce bright values near polyps because they have similar shapes, can be used to detect and estimate the size and structures of polyp candidates.

The sphere and hemisphere-based responses are calculated by first selecting a location in the distance transformed image and recording the distance value at that location. A set of rays are then projected radially outward from the selected location, and a distance value is measured for each ray that is a fraction (e.g., approximately three-quarters) of the distance from the selected location (i.e., its origin distance). The resulting data is composed of a series of ray lengths (where each ray has a partner in a supplementary direction), and these lengths are used in the computation of the sphere and hemisphere responses.

After the ray lengths have been determined, the sphere-based response is calculated. First, a scale of the sum of the difference of the original value (i.e., the selected location in the image) minus the values of the individual rays, which are a fraction from the distance of the selected location, if the length values are less than the original, is computed. The sum is then divided by the total number of rays cast radially outward from the selected location and a final value is determined. The sphere-based response is calculated using Equation (2) shown below:

$$\frac{\sum_{i \in S}(d - l_i)}{T} \quad (2)$$

where d is the original distance value (of the selected location), $l_i$ is the length of a ray i, T is the total number of rays, and S is the set of rays such that $l_i < d$.

The hemisphere-based response is calculated similar to that of the sphere response. However, when calculating the hemisphere response, if supplementary rays have distance values less than the original distance value, they are not included in the sum. Yet, if one of the rays has a distance value less than the original distance value, both rays are included in the final sum. The sum is then divided by half of the total number of rays as shown in Equation (3) below:

$$\frac{\sum_{i \in S}(d - l_i)}{T/2} \quad (3)$$

where S is the set of rays whose supplementary rays do not have a value less than the original value, d is the original distance value, $l_i$ is the length of a ray i, and T is the total number of rays.

It is to be understood that the sphere and hemisphere-based responses can be used interchangeably and independent of each other and that they can be used to supplement the processing in step 225 or they can be used in combination or singular in place of the previously described processing for step 225.

Figure 5:
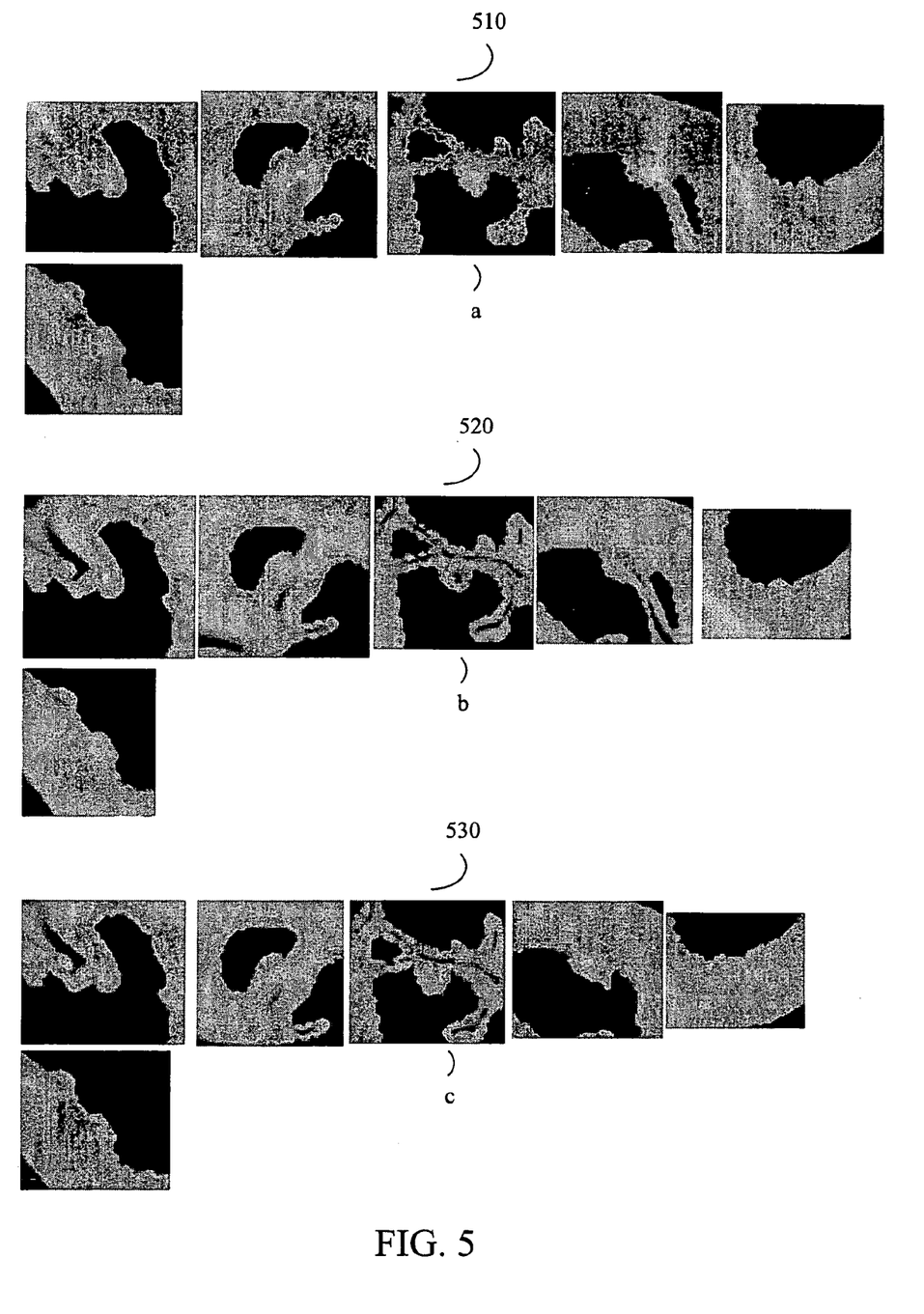
FIG. 5 illustrates 3D medical images of a colon processed according to an exemplary embodiment of the present invention.

FIG. 5 illustrates 3D medical images of a colon processed according to an exemplary embodiment of the present invention. As shown in FIG. 5, a set of images 510 illustrate several portions of the colon that have undergone the first processing described with reference to step 225. Image (a) illustrates a candidate polyp that is identified by the downward facing protrusion in the center of the image (a). A set of images 520 illustrate the same portions of the colon as shown in the image 510 that have been processed using a hemisphere-based response. Image (b) illustrates the same candidate polyp as shown in the image (a). A set of images 530 illustrate the minimum values of the images 510 and 520 after the high center and hemisphere values are removed.

More specifically, the image 530 is computed by taking the minimum response of the images (a) and (b). As a result, image (c), which is the resulting polyp candidate, is brighter and more clearly defined than the same candidate polyp of images (a) and (b) affording easier polyp detection for a user and/or a conventional CAD detecting/filtering system.

Figure 6:
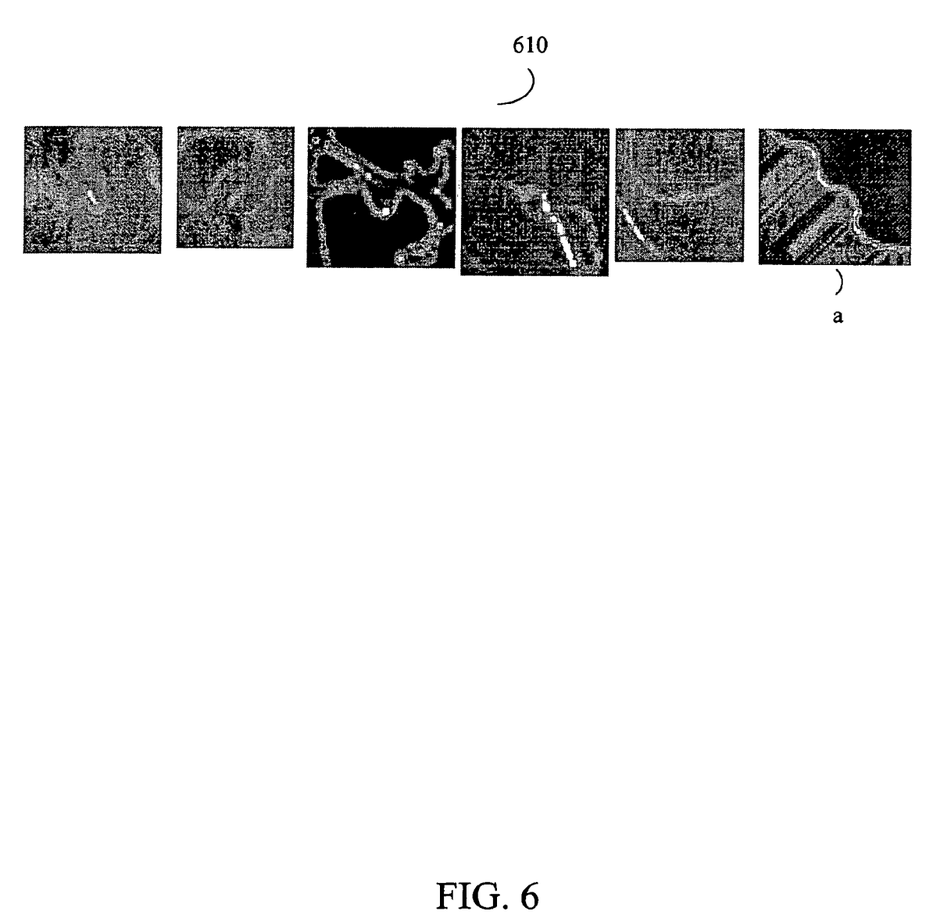
FIG. 6 illustrates 3D medical images of a colon processed according to another exemplary embodiment of the present invention.

FIG. 6 illustrates 3D medical images of a colon processed according to another exemplary embodiment of the present invention. As shown in FIG. 6, a set of images 610 illustrate several portions of the colon that have been processed using an accumulated gradient following technique. Processing using the accumulated gradient following technique is done by casting a line from the edge of a distance transformed image that follows the steepest calculated gradient. As each line follows the steepest gradient, it adds a value of "1" to the response image, and as multiple lines are cast, their paths accumulate at points within the image. In this method, polyp locations tend to have a prominent line structure as a response. Thus, candidate polyps can be detected by observing protruding regions with bright line-like structures as shown in image (a) of FIG. 6.

Figure 7:
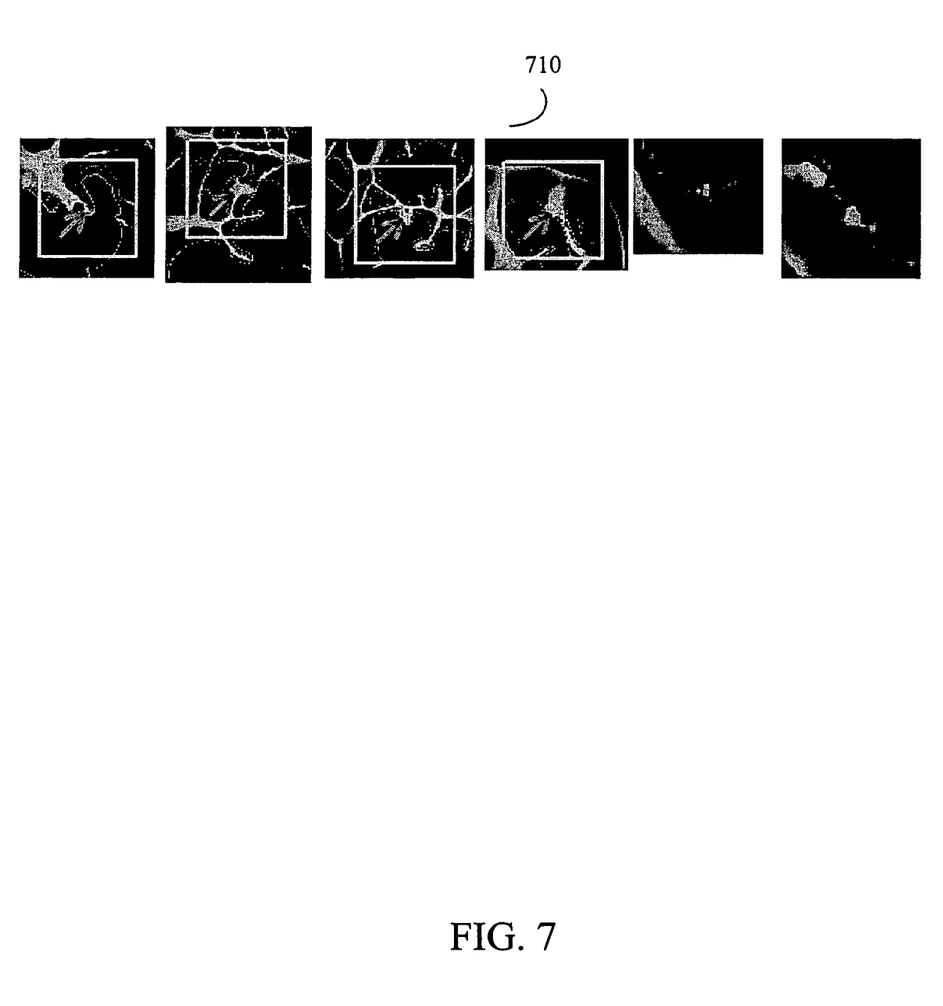
FIG. 7 illustrates 3D medical images of a colon processed according to yet another exemplary embodiment of the present invention.

FIG. 7 illustrates 3D medical images of a colon processed according to yet another exemplary embodiment of the present invention. As shown in FIG. 7, a set of images 710 illustrate several portions of the colon that have been processed using a continuous gray-level difference technique.

Similar to the sphere-based response, the continuous gray-level difference technique begins by casting a set of rays outward from a selected location in a distance transformed image. Along select points in each ray, the absolute value of the distance value minus the length of each ray at that point is taken. The total of these differences is divided by the total number of points sampled, and the sum of each of these values is divided by the total number of rays. The final value approaches zero for perfect spheres and is greater than zero for non-spherical objects. This value is then subtracted from a positive constant to invert the values so that spherical objects have the greater values.

In the continuous gray-level technique, each ray is computed as shown in Equation (4):

$$\frac{\sum_{i=0}^{F \times d} |d_i - l_i|}{T} \quad (4)$$

where d is the distance label at the origin, F is a fraction value between 0 and 1, di is the distance value at the specific point along the ray, $l_i$ is the length of the ray at point i, and T is the total number of points taken from i=0 to i=F*d.

After each ray has been calculated using Equation (4), the final value is computed using Equation (5):

$$\frac{\sum_{i=0}^{K} r_k}{K} \quad (5)$$

where rk represents the value computed by Equation (4) for each ray k. The resulting image formed by using the gray-level difference technique enables polyp candidates to be detected by observing the bright spherical portions in the resulting set of images 710.

It is to be understood that a hemisphere-based response can also be calculated using the continuous gray-level technique described above and the minimum values from the hemisphere and sphere-based responses can be taken to produce an image for determining polyp candidates.

In accordance with the present invention, the locations of candidate polyps in, for example, a colon can be detected by taking a distance transform of a segmented medical image and processing its gradient characteristics. In addition, the size and/or shapes of candidate polyps can also be estimated using the processing methods described herein, by observing that a distance label and/or value at a location (e.g., where a candidate polyp has been detected) in a distance transformed image can be used to estimate the size of a polyp. In addition, a statistical measure of the distance labels can be used to estimate the size of a polyp in a detected region. Accordingly, conventional CAD systems can be enhanced by employing the present invention to increase accuracy, and to reduce cost and analysis time associated with the interpretation of medical conditions such as colonic polyps in medical images.

It is to be understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

It should also be understood that the above description is only representative of illustrative embodiments. For the convenience of the reader, the above description has focused on a representative sample of possible embodiments, a sample that is illustrative of the principles of the invention. The description has not attempted to exhaustively enumerate all possible variations. That alternative embodiments may not have been presented for a specific portion of the invention, or that further undescribed alternatives may be available for a portion, is not to be considered a disclaimer of those alternate embodiments. Other applications and embodiments can be straightforwardly implemented without departing from the spirit and scope of the present invention. It is therefore intended, that the invention not be limited to the specifically described embodiments, because numerous permutations and combinations of the above and implementations involving non-inventive substitutions for the above can be created, but the invention is to be defined in accordance with the claims that follow. It can be appreciated that many of those undescribed embodiments are within the literal scope of the following claims, and that others are equivalent.

What is claimed is:

1. A method for detecting a protrusion in a medical image, comprising:
    segmenting a medical image;
    calculating a distance map of the medical image;
    calculating a gradient of the distance mapped medical image; and
    processing the gradient to detect a protrusion in the medical image, wherein the gradient is processed by:
    projecting a first plurality of rays from a location in the distance mapped medical image;
    calculating a value for each of the first plurality of rays based on features of each of the first plurality of rays and the gradient of the distance mapped medical image;
    summing and scaling the value of each of the first plurality of rays; and
    detecting one of a sphere-like and polyp-like shape using the summed and scaled values of the first plurality of rays, wherein one of the sphere-like and polyp-like shapes is the protrusion.

2. The method of claim 1, farther comprising:
    acquiring the medical image.

3. The method of claim 2, wherein the medical image is acquired by one of a computed tomographic (CT), helical CT, x-ray, positron, emission tomogaphic, fluoroscopic, ultrasound, and magnetic resonance (MR) imaging technique.

4. The method of claim 2, wherein the medical image is of an anatomical part.

5. The method of claim 1, wherein the processing step further comprises:
    projecting a second plurality of rays from a location comprising an original distance value in the distance mapped medical image;
    calculating an absolute value of a difference between a length of each of the second plurality of rays and a distance value at an end of each of the second plurality of rays, wherein the length of each of the second plurality of rays is a fraction of the original distance value from the location;
    dividing a sum of the absolute value by the total number of the second plurality of rays; and
    detecting one of a sphere-like and polyp-like shape using the division result, wherein one of the sphere-like and polyp-like shapes is the protrusion.

6. The method of claim 1, wherein the processing step further comprises:
    projecting a second plurality of rays from a location comprising an original distance value in the distance mapped medical image;
    determining a distance value for each of the second plurality of rays that is a fraction of the original distance value from the location;
    calculating a sphere-based response, wherein the sphere-based response is calculated by:

$$\frac{\sum_{i \in S}(d - l_i)}{T}$$

where d is the original distance value, $l_i$ is the length of a ray i, T is a total number of the second plurality of rays, and S is a set of the second plurality of rays such that $l_i < d$; and
    detecting the protrusion using the sphere-based response.

7. The method of claim 1, wherein the processing step further comprises:
    projecting a second plurality of rays from a location comprising an original distance value in the distance mapped medical image;
    determining a distance value for each of the second plurality of rays that has a supplementary ray that has a distance value less than the original distance value;
    calculating a hemisphere-based response; wherein the hemisphere-based response is calculated by:

$$\frac{\sum_{i \in S}(d - l_i)}{T/2}$$

where d is the original distance value, $l_i$ is the length of a ray i, T is a total number of the second plurality of rays, and S is a set of the second plurality of rays whose supplementary rays do hot have a value less than the original distance value; and
detecting the protrusion using the hemisphere-based response.

8. The method of claim 1, wherein the processing step further comprises:
projecting a second plurality of rays from an edge of the distance mapped medical image, wherein the second plurality of rays follow the steepest gradient; and
accumulating paths of the second plurality of rays, wherein the accumulated paths form a response image for detecting the protrusion.

9. The method of claim 1, wherein the processing step further comprises:
projecting a second plurality of rays from a location comprising an original distance value in the distance mapped medical image;
determining a distance value for each of the second plurality of rays that is a fraction of the original distance value from the location;
calculating a sphere-based response, wherein the sphere-based response is calculated by:

$$\frac{\sum_{i=0}^{F \times d}|d_i - l_i|}{T}$$

where d is the original distance value, F is a fractional value between 0 and 1, dis the distance value at a point along one of the second plurality of rays, $l_i$ is the length of one of the second plurality of rays at a point i, and T is the total number of points taken from i=0 to i=F*d;
calculating a gray-level difference of the distance mapped medical image, wherein the gray level difference is calculated by:

$$\frac{\sum_{i=0}^{K} r_k}{K}$$

where rk represents the sphere-based response for each ray k; and
detecting the protrusion using the gray-level difference.

10. The method of claim 1, wherein the protrusion is one of a nodule, lesion, polyp, pre-cancerous growth, and cancerous growth.

11. The method of claim 1, further comprising:
storing a list of one or more detected protrusions; and
filtering one or more false positives from the list, wherein one of the false positives is not one of a nodule, lesion, polyp, pre-cancerous growth, and cancerous growth.

12. A system for detecting a protrusion in a medical image, comprising:
a memory device for storing program code;
a processor in communication with the memory device, the processor operative with the program code to:
segment a medical image;
calculate a distance map of the medical image;
calculate a gradient of the distance mapped medical image; and
process the gradient to detect a protrusion in the medical image, wherein when processing the gradient, the processor is operative with the program code to:
project a first plurality of rays from a location in the distance mapped medical image;
calculate a value for each of the first plurality of rays based on features of each of the first plurality of rays and the gradient of the distance mapped medical image;
summing and scaling the value for each of the first plurality of rays; and
detecting one of a sphere-like and polyp-like shape using the summed and scaled values of the first plurality of rays, wherein one of the sphere-like and polyp-like shapes is the protrusion.

13. The system of claim 12, wherein the processor is further operative with the program code to:
acquire the medical image, wherein the medical image is of an anatomical part.

14. The system of claim 13, wherein the medical image is acquired by one of a computed tomographic (CT), helical CT, x-ray, positron emission tomographic, fluoroscopic, ultrasound, and magnetic resonance (MR) imaging technique.

15. The system of claim 12, wherein the processor is further operative with the program code when processing the gradient to:
project a second plurality of rays from a location comprising an original distance value in the distance mapped medical image;
calculate an absolute value of a difference between a length of each of the second plurality of rays and a distance value at an end of each of the second plurality of rays, wherein the length of each of the second plurality of rays is a fraction of the original distance value from the location;
divide a sum of the absolute value by the total number of the second plurality of rays; and
detect one of a sphere-like and polyp-like shape using the division result, wherein one of the sphere-like and polyp-like shapes is the protrusion.

16. The system of claim 12, wherein the processor is further operative with the program code when processing the gradient to:
project a second plurality of rays from a location comprising an original distance value in the distance mapped medical image;
determine a distance value for each of the second plurality of rays that is a fraction of the original distance value from the location;
calculate a sphere-based response of the second plurality of rays;
calculate a hemisphere-based response of the second plurality of rays; and
detect the protrusion using the sphere and hemisphere-based responses.

17. The system of claim 12, wherein the processor is further operative with the program code when processing the gradient to:

project a second plurality of rays from an edge of the distance mapped medical image, wherein the second plurality of rays follow the steepest gradient; and accumulate paths of the second plurality of rays, wherein the accumulated paths form a response image for detecting the protrusion.

18. The system of claim 12, wherein the processor is further operative with the program code when processing the gradient to:

project a second plurality of rays from a location comprising an original distance value in the distance mapped medical image;

determine a distance value for each of the second plurality of rays that is a fraction of the original distance value from the location;

calculate a sphere-based response of the second plurality of rays;

calculate a gray-level difference of the distance mapped medical image; and detect to protrusion using to sphere-based response and the gray-level difference.

19. The system of claim 12, wherein the protrusion is one of a nodule, lesion, polyp, pre-cancerous growth, and cancerous growth.

20. The system of claim 12, wherein the processor is further operative with the program code when processing the gradient to:

store a list of one or more detected protrusions; and filter one or more false positives from the list, wherein one or more of the false positives is not one of a nodule, lesion, polyp, pre-cancerous growth, and cancerous growth.

21. A computer program product comprising a computer useable medium having computer program logic recorded thereon for detecting a protrusion in a medical image, the computer program logic comprising:

program code for segmenting a medical image;

program code for calculating a distance map of the medical image;

program code for calculating a gradient of the distance mapped medical image; and program code for processing the gradient to detect a protrusion in the medical image, wherein the gradient is processed by;

projecting a plurality of rays from a location in the distance mapped medical image;

calculating a value for each of the plurality of rays based on features of each of the plurality of rays and the gradient of the distance mapped medical image;

summing and scaling the value of each of the plurality of rays; and detecting one of a sphere-like and polyp-like shape using the summed and scaled values of the plurality of rays, wherein one of the sphere-like and polyp-like shapes is the protrusion.

22. The computer program product of claim 21, further comprising:

program code for acquiring the medical image.

23. The system computer program product of claim 22, wherein the image is acquired by one of a computed tomographic (CT), helical CT, x-ray, positron emission tomographic, fluoroscopic, ultrasound, and magnetic resonance (MR) imaging technique.

24. The computer program product of claim 21, wherein the protrusion is one of a nodule, lesion, polyp, pre-cancerous growth, and cancerous growth.

25. A method for detecting a protrusion in a medical image, comprising:

segmenting a medical image;

calculating a distance map of the medical image;

calculating a gradient of the distance mapped medical image; and processing the gradient to detect a protrusion in the medical image, wherein the gradient is processed by:

projecting a plurality of rays from a location comprising an original distance value in the distance mapped medical image;

calculating an absolute value of a difference between a length of each of the plurality of rays and a distance value at an end of each of the plurality of rays, wherein the length of each of the plurality of rays is a fraction of the original distance value from the location;

dividing a sum of the absolute value by the total number of the plurality of rays; and detecting one of a sphere-like and polyp-like shape using the division result, wherein one of the sphere-like and polyp-like shapes is the protrusion.

26. A method for detecting a protrusion in a medical image, comprising:

segmenting a medical image;

calculating a distance map of the medical image;

calculating a gradient of the distance mapped medical image; and processing the gradient to detect a protrusion in the medical image, wherein the gradient is processed by using first, second or third techniques:

wherein the first technique includes:

projecting a plurality of rays from a location comprising an original distance value in the distance mapped medical image;

determining a distance value for each of the plurality of rays that is a fraction of the original distance value from the location;

calculating a sphere-based response of the plurality of rays; and detecting the protrusion using the sphere-based response;

wherein the second technique includes:

projecting plurality of rays from a location comprising an original distance value in the distance mapped medical image;

determining a distance value for each of the plurality of rays that is a fraction of the original distance value from the location;

calculating a sphere-based response of the plurality of rays;

calculating a gray-level difference of the distance mapped medical image; and detecting the protrusion using the gray-level difference;

wherein the third technique includes:

projecting a plurality of rays from a location comprising an original distance value in the distance mapped medical image;

determining a distance value for each of the plurality of rays that has a supplementary ray that has a distance value less than the original distance value;

calculating a hemisphere-based response of the plurality of rays; and detecting the protrusion using the hemisphere-based response.

* * * * *